United States Patent [19]

Regel et al.

[11] 4,381,306

[45] Apr. 26, 1983

[54] HYDROXYPROPYL-TRIAZOLE COMPOUNDS, THEIR PRODUCTION AND THEIR MEDICINAL USE

[75] Inventors: Erik Regel; Karl H. Büchel; Ingo Haller; Manfred Plempel, all of Wuppertal, Fed. Rep. of Germany

[73] Assignee: Bayer Aktiengesellschaft, Leverkusen, Fed. Rep. of Germany

[21] Appl. No.: 92,805

[22] Filed: Nov. 9, 1979

[30] Foreign Application Priority Data

Nov. 25, 1978 [DE] Fed. Rep. of Germany ....... 2851086

[51] Int. Cl.³ .................... A61K 31/41; C07D 249/08
[52] U.S. Cl. .................................. 424/269; 548/262; 424/232
[58] Field of Search .......................... 548/262; 424/269

[56] References Cited

U.S. PATENT DOCUMENTS 4,113,465  9/1978  Shephard et al. ............. 424/273 R

FOREIGN PATENT DOCUMENTS 2623129 11/1977 Fed. Rep. of Germany ...... 548/341
1464224  2/1977 United Kingdom ............... 548/262

*Primary Examiner*—Alton D. Rollins
*Attorney, Agent, or Firm*—Sprung, Horn, Kramer & Woods

[57] ABSTRACT

The invention relates to hydroxypropyl-triazole compounds and methods for their preparation. Also included are compositions containing said hydroxypropyl-triazoles and methods for the use of the said active compounds and compositions, as antimycotic agents.

16 Claims, No Drawings

HYDROXYPROPYL-TRIAZOLE COMPOUNDS, THEIR PRODUCTION AND THEIR MEDICINAL USE

The present invention relates to certain new hydroxy-propyl-triazole compounds, to processes for their production and to their use as antimycotic agents.

It has already been disclosed that hydroxy-triazolylalkanes, such as, for example, 4,4-dimethyl-3-hydroxy-2-phenoxy-1-(1,2,4-triazol-1-yl)-pentane derivatives substituted in the phenyl part, have a good antimycotic action (compare DE-OS (German Published Specification) 2,350,121). However, their reaction is not always completely satisfactory, especially against dermatophytes.

According to the present invention there are provided compounds which are hydropropyltriazoles of the general formula

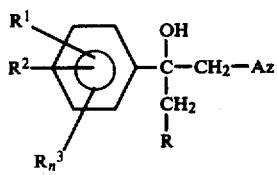

or a salt thereof in which
  Az denotes a triazole radical,
  R denotes an optionally substituted phenyl, naphthyl or tetrahydronaphthyl radical
  $R^1$ denotes an optionally substituted phenyl or cycloalkyl radical and
  $R^2$ denotes a hydrogen atom, or
  $R^1$ and $R^2$ together, in the o-position relative to one another, denote an optionally substituted methylene bridge with more than one member, or, together with the phenyl ring, complete a naphthyl radical,
  $R^3$ denotes a halogen atom or an alkyl, alkoxy or halogeno-alkyl group and
  n is 0, 1, 2 or 3.

The compounds of the present invention have powerful antimycotic properties.

According to the present invention there is further provided a process for the production of compounds of the present invention in which
(a) a triazolylmethyl phenyl ketone of the general formula

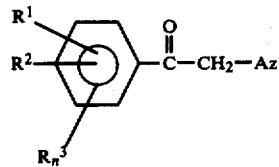

in which
  Az, $R^1$, $R^2$, $R^3$ and n have the meaning indicated above,
is reacted with a Grignard compound of the general formula

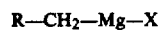

R—CH$_2$—Mg—X (III)

in which

R has the meaning indicated above and
X denotes a halogen atom, preferably a chlorine or bromine atom,
in the presence of a diluent or
(b) a 1-halogen-propan-2-ol of the general formula

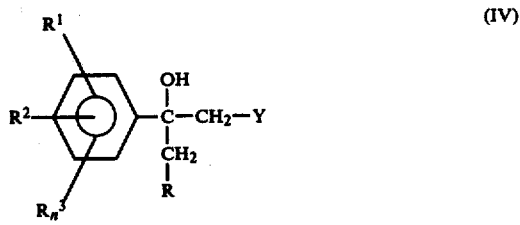

in which
  R, $R^1$, $R^2$, $R^3$ and n have the meaning indicated above and
  Y denotes a halogen atom, preferably a chlorine or bromine atom,
is reacted with triazole or an alkali metal salt thereof, preferably in the presence of an acid-binding agent and preferably in the presence of a diluent; and the product of reaction variant (a) or (b) is, if desired, converted into a salt by reaction with an acid. In some cases it proves advantageous to use the triazole in the form of the alkali metal salt, such as the sodium salt or potassium salt.

The hydroxypropyl-triazoles of the formula (I) obtainable according to the invention can furthermore be converted into salts by reaction with acids. Among the new hydroxy-propyl-triazole salts of the invention, those salts that are pharmaceutically acceptable, as has been indicated above, are particularly important and are preferred.

Surprisingly, the hydroxypropyl-triazoles according to the invention exhibit a better, therapeutically usable activity, especially against dermatophytes, than the known hydroxy-triazolyl-alkanes which are closely related compounds such as, for example, 4,4-dimethyl-3-hydroxy-2-phenoxy-1-(1,2,4-triazol-1-yl)-pentane derivatives substituted in the phenyl part. The active compounds according to the invention thus represent a valuable advance in pharmacy.

Preferred hydroxypropylazoles of the present invention are those in which Az denotes a 1,2,4-triazol-1-yl or 1,3,4-triazol-1-yl radical; R denotes an optionally substituted (preferably mono- or di-substituted) phenyl, naphthyl or tetrahydronaphthyl radical, preferred substituents which may be mentioned being: halogen, preferably fluorine, chlorine and bromine, straight-chain or branched alkyl and alkoxy with in each case 1 to 4 carbon atoms, and halogenoalkyl with 1 to 4 carbon atoms and up to 5 halogen atoms, preferably with 1 or 2 carbon atoms and up to 3 identical or different halogen atoms, halogens being, preferably fluorine and chlorine and trifluoromethyl being mentioned as an example; $R^1$ denotes an optionally substituted (preferably nono- or di-substituted) phenyl or $C_3$ to $C_7$ cycloalkyl radical, preferred substituents which may be mentioned being: halogen, preferably fluorine, chlorine or bromine, and alkyl with 1 to 4, preferably with 1 to 5 carbon atoms, and $R^2$ denotes a hydrogen atom, or $R^1$ and $R^2$ together, in the ortho-position relative to one another, denote a methylene bridge which has 3 to 5 methylene groups and is optionally monosubstituted or polysubstituted (such as di-substituted), preferred substituents which may be mentioned being: halogen, preferably fluorine, chlorine or bromine, and alkyl with 1 to 4, preferably with 1 to 2 carbon atoms, or $R^1$ and $R^2$ together with the phenyl ring, complete a naphthyl radical; $R^3$ denotes a halogen atom, preferably fluorine, chlorine or bromine, a straight-chain or branched alkyl or alkoxy group with in each case 1 to 4 carbon atoms, or a halogenoalkyl group with 1 to 4 carbon atoms and up to 5 halogen atoms, preferably with 1 or 2 carbon atoms and up to 3 identical or different halogen atoms, halogens being, preferably fluorine and chlorine, and trifluoromethyl and 1,1,1-trifluoroethyl being mentioned as examples; and n is 0, 1, or 2.

Very particularly preferred compounds of the present invention are those in which Az has the meaning indicated above; R denotes a phenyl radical which is optionally monosubstituted or disubstituted by chlorine, fluorine or methyl, or denotes a naphthyl or tetrahydronaphthyl radical; $R^1$ denotes a phenyl, cyclopentyl or cyclohexyl radical, which is optionally monosubstituted or disubstituted by chlorine, bromine, fluorine or methyl, and $R^2$ denotes a hydrogen atom, or $R^1$ and $R^2$ together, in the ortho-position relative to one another, denote a trimethylene, tetramethylene or pentamethylene bridge which is optionally substituted by chlorine or methyl, or, together with the phenyl ring, complete a naphthyl radical; $R^3$ denotes a chlorine or fluorine atom or a methyl group; and n represents 0 or 1.

The following compounds of the general formula (I) (in which Az in each case represents 1,2,4- or 1,3,4-triazol-1-yl) may be mentioned specifically, in addition to the compounds mentioned in the preparation examples:

General structure:

$R^2$—(phenyl ring with $R^1$, $R_n^3$ substituents)—C(OH)(CH$_2$—Az)(CH$_2$R)

| R | $R^1$ | $R^2$ | $R_n^3$ |
|---|---|---|---|
| 4-Cl-C$_6$H$_4$- | 4-H-C$_6$H$_4$- (phenyl) | H | — |
| 3,4-Cl$_2$-C$_6$H$_3$- | phenyl | H | — |
| 3-F-4-Cl-C$_6$H$_3$- | phenyl | H | — |
| 3,4-Cl$_2$-C$_6$H$_3$- | phenyl | H | — |
| 3-Cl-C$_6$H$_4$- | phenyl | H | — |
| 2-Cl-C$_6$H$_4$- | phenyl | H | — |

-continued

| R | $R^1$ | $R^2$ | $R_n^3$ |
|---|---|---|---|
| 4-Cl-C$_6$H$_4$- | 4-H-C$_6$H$_4$- | H | — |
| 4-Cl-C$_6$H$_4$- | — | 3,4-(CH$_2$)$_3$- | — |
| 4-Cl-C$_6$H$_4$- | — | 3,4-(CH$_2$)$_4$- | — |
| phenyl | 4-Cl-C$_6$H$_4$- | H | — |
| 4-F-C$_6$H$_4$- | 4-C$_6$H$_5$ | H | — |
| 2-Cl-C$_6$H$_4$- | 4-Cl-C$_6$H$_4$- | H | — |
| 4-F-C$_6$H$_4$- | 4-Cl-C$_6$H$_4$- | H | — |
| 2,4-Cl$_2$-C$_6$H$_3$- | 4-Cl-C$_6$H$_4$- | H | — |
| 4-Cl-C$_6$H$_4$- | 2-Cl-C$_6$H$_4$- | H | — |
| phenyl | 2-Cl-C$_6$H$_4$- | H | — |
| 4-Cl-C$_6$H$_4$- | 2,4-Cl$_2$-C$_6$H$_3$- | H | — |
| 4-F-C$_6$H$_4$- | 2-Cl-C$_6$H$_4$- | H | — |
| 4-F-C$_6$H$_4$- | 2,4-Cl$_2$-C$_6$H$_3$- | H | — |
| 2,4-Cl$_2$-C$_6$H$_3$- | 2-Cl-C$_6$H$_4$- | H | — |

-continued

| R | R¹ | R² | R_n³ |
|---|----|----|------|
| 3,4-di-Cl-C₆H₃ | 4-Cl-C₆H₄ | H | — |
| 3,4-di-Cl-C₆H₃ | 4-Cl-C₆H₄ | H | — |
| 3,4-di-Cl-C₆H₃ | 4-Cl-C₆H₄ | H | — |
| 3,4-di-Cl-C₆H₃ | 4-Cl-C₆H₄ | H | — |
| 3,4-di-Cl-C₆H₃ | 4-Cl-C₆H₄ | H | — |
| 2-naphthyl | 4-C₆H₅ | H | — |
| 2-naphthyl | 4-C₆H₅ | H | — |
| 3,4-di-Cl-C₆H₃ | 4-C₆H₅ | H | — |
| 3,4-di-Cl-C₆H₃ | 3,4-(CH₂)₄— | — | — |
| 3,4-di-Cl-C₆H₃ | 3,4-(CH₂)₃— | — | — |
| 3,4-di-Cl-C₆H₃ | 4-cyclopentyl | H | — |
| 4-F-C₆H₄ | 4-F-C₆H₄ | H | — |
| 4-F-C₆H₄ | 4-C₆H₅ | H | — |

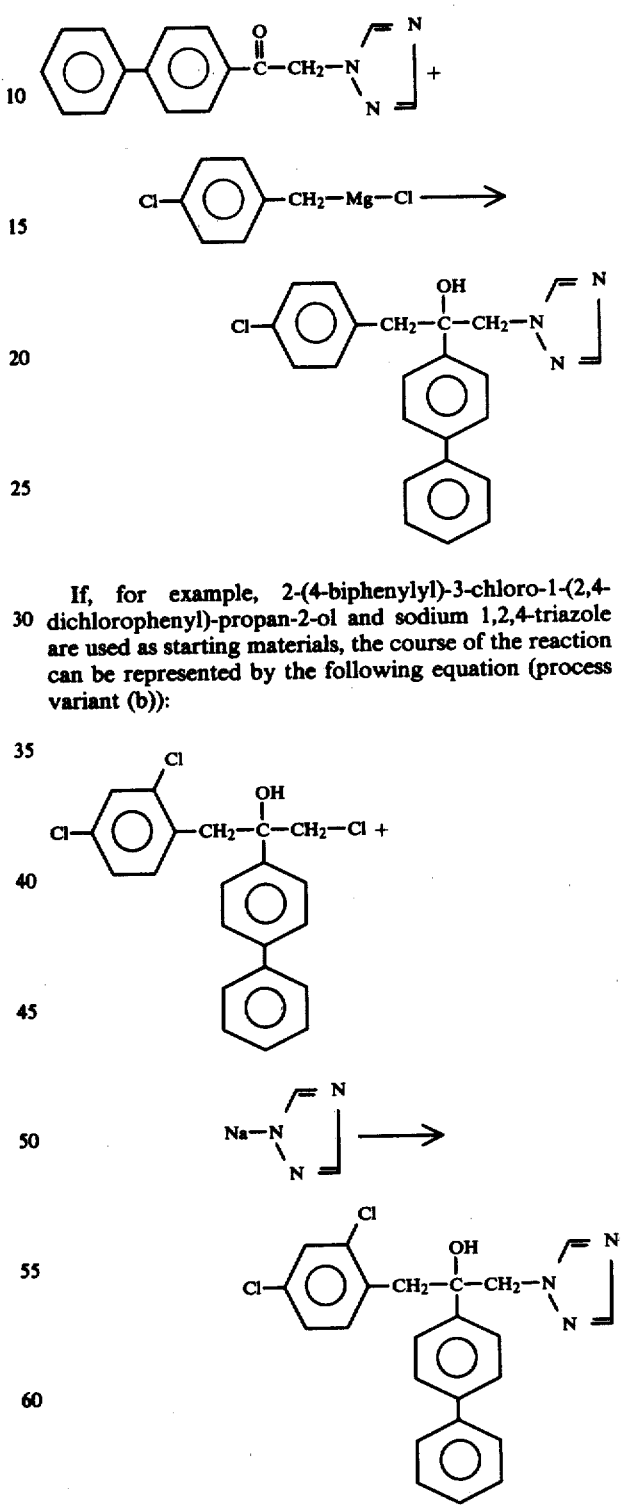

If for example, 4-biphenyl 1,2,4-triazol-1-yl methyl ketone and 4-chlorobenzyl-magnesium chloride are used as starting materials, the course of the reaction can be represented by the following equation (process variant (a)):

If, for example, 2-(4-biphenylyl)-3-chloro-1-(2,4-dichlorophenyl)-propan-2-ol and sodium 1,2,4-triazole are used as starting materials, the course of the reaction can be represented by the following equation (process variant (b)):

Preferred compounds of formula (II) to be used as starting materials for process variant (a) are those in which Az, R¹, R², R³ and n have the meanings indicated for the mentioned preferred and very particularly preferred hydroxypropylazoles of the invention.

The triazolylmethyl phenyl ketones of the formula (II) are novel. However, they can be prepared in a known manner by reacting corresponding phenacyl halides of the formula

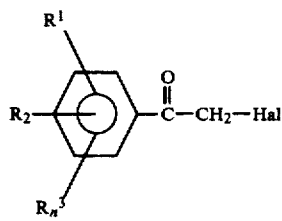

in which
R$^1$, R$^2$, R$^3$ and n have the meaning indicated above and
Hal denotes a chlorine or bromine atom,
with a triazole in the presence of a diluent, such as, for example, dimethylformamide, and in the presence of an acid-binding agent, such as, in particular, an excess of azole, at temperatures between 20° and 80° C. (in this context, compare also the statements in U.S. Pat. No. 3,658,813).

Examples of the starting substances of the formula (II) which may be mentioned are: 4-biphenylyl 1,2,4- or 1,3,4-triazol-1-yl-methyl ketone, 4-(4'-chlorobiphenylyl) 1,2,4- or 1,3,4-triazol-1-yl-methyl ketone, 2-biphenylyl 1,2,4- or 1,3,4-triazol-1-yl-methyl ketone, 4-(2',4'-dichlorobiphenylyl) 1,2,4- or 1,3,4-triazol-1-yl-methyl ketone, 2-chloro-4-biphenylyl 1,2,4- or 1,3,4-triazol-1-yl-methyl ketone, 2-chloro-4-(4'-chlorobiphenylyl) 1,2,4-triazol- or 1,3,4-triazol-1-yl-methyl ketone, 4-cyclohexylphenyl 1,2,4-triazol- or 1,3,4-triazol-1-yl-methyl ketone, 4-cyclopentylphenyl 1,2,4-triazol- or 1,3,4-triazol-1-yl-methyl ketone, 4-chloro-3-cyclohexylphenyl 1,2,4-triazol- or 1,3,4-triazol-1-yl-methyl ketone, 4-(3-bromocyclohexyl)-phenyl 1,2, 4-triazol- or 1,3,4-triazol-1-ylmethyl ketone, 4-cyclopentyl-2-chlorophenyl 1,2,4-triazol- or 1,3,4-triazol-1-yl-methyl ketone, 4-cyclopentyl-2-fluorophenyl 1,2,4-triazol- or 1,3,4-triazol-1-yl-methyl ketone, 4-cyclopentyl-2-methyl phenyl 1,2,4-triazol- or 1,3,4-triazol-1-yl-methyl ketone, 4-(1-methylcyclohexy)-phenyl 1,2,4-triazol- or 1,3,4-triazol-1-yl-methyl ketone, 4-cycloheptylphenyl 1,2,4-triazol- or 1,3,4-triazol-1-yl-methyl ketone, 4-cycloheptyl-2-chlorophenyl 1,2,4-triazol- or 1,3,4-triazol-1-yl-methyl ketone, naphth-1-yl 1,2,4-triazol- or 1,3,4-triazol-1-yl-methyl ketone, naphth-2-yl 1,2,4-triazol- or 1,3,4-triazol-1-yl-methyl ketone, 1,2,3,4-tetrahydronaphth-5-yl 1,2,4-triazol- or 1,3,4-triazol-1-yl-methyl ketone, 1,2,3,4-tetrahydro-naphth-6-yl 1,2,4-triazol- or 1,3,4-triazol-1-yl-methyl ketone and indan-4-yl 1,2,4-triazol or 1,3,4-triazol-1-yl-methyl ketone.

Preferred Grignard compounds of formula (III) are used as starting material for process variant (a) are those in which R has the meaning indicated for the mentioned preferred and very particularly preferred hydroxy-propylazoles of the invention.

The Grignard compounds of the formula (III are generally known compounds of organic chemistry. Examples which may be mentioned are: benzyl-magnesium chloride, 4-chlorobenzyl-magnesium chloride, 2,4-dichlorobenzyl-magnesium chloride, 2,6-dichlorobenzyl-magnesium chloride, 2-chloro-6-fluorobenzyl-magnesium chloride, 2-chlorobenzyl-magnesium chloride, 3-chlorobenzyl-magnesium chloride, 3,4-dichlorobenzyl-magnesium chloride, naphth-2-yl-methyl-magnesium chloride and 1,2,3,4-tetrahydronaphth-6-yl-methyl-magnesium chloride, and the corresponding bromides.

Preferred 1-halogenopropan-2-ols of formula (IV) to be used as starting material for process variant (b) are those in which R, R$^1$, R$^2$, R$^3$ and n have the meanings indicated for the mentioned preferred and very particularly preferred hydroxy-propylazoles of the invention.

The 1-halogenpropan-2-ols of the formula (IV) are novel. However, they can be prepared in a known manner by reacting ketones of the formula (VI) with Grignard compounds of the formula (III) according to process variant (a) (in this context, compare also the statements of DE-OS (German Published Specification) 2,623,129 and the preparation examples, corresponding to British Pat. No. 1,532,156).

All the solvents customary for a Grignard reaction can be used as the diluent for the reaction, according to the invention, in process variant (a). Preferred solvents include ethers, such as diethyl ether or tetrahydrofurane, and mixtures with other organic solvents, such as, for example benzene.

The reaction temperatures can be varied within a substantial range in process variant (a). The reaction is preferably carried out between 20° and 120° C., more preferably between 30° and 80° C.

An excess of the Grignard compound of the formula (III) of 3 to 5 mols is preferably employed per 1 mol of the compound of the formula (II) in carrying out process (a). Isolation of the compounds of the formula (I) is effected in known manner.

Preferred possible diluents for the reaction, according to the invention, in process variant (b) are inert organic solvents. Preferred solvents include ketones, such as diethyl ketone, and in particular acetone and methyl ethyl ketone, nitriles, such as propionitrile, and in particular acetonitrile, alcohols, such as ethanol or isopropanol; ethers, such as tetrahydrofurane or dioxane; aromatic hydrocarbons, such as benzene, toluene and dichlorobenzene; formamides, such as, in particular, dimethylformamide; and halogenated hydrocarbons, such as methylene chloride, carbon tetrachloride or chloroform.

If process variant (b) according to the invention is carried out in the presence of an acid-binding agent, it is possible to add any of the inorganic or organic acid-binding agents which can customarily be used, such as alkali metal carbonates, for example sodium carbonate, potassium carbonte and sodium bicarbonate, or such as lower tertiary alkylamines, cycloalkylamines or aralkylamines, for example triethylamine, N,N-dimethylcyclohexylamine, dicyclohexylmethylamine and N,N-dimethylbenzylamine, and furthermore pyridine and diazabicyclooctane. The said alkylamines preferably contain 1 to 6 carbon atoms, the said cycloalkylamines preferably are these having 4 to 9 ring members and said aralkylamines are preferably benzenoid in the aromatic portion and contains 1 to 2 carbon atoms in the alkyl portion. An excess of azole is preferably used.

The reaction temperatures can be varied within a substantial range in process variant (b). The reaction is preferably carried out between 30° and 200° C., more preferably at the boiling point of the solvent.

1 to 2.5 mols of azole and 1 to 2.5 mols of acid-binding agent are preferably employed per 1 mol of the compounds of the formula (IV) in carrying out process variant (b) according to the invention. If an alkali metal salt is used, 1 to 1.5 mols thereof are preferably employed per 1 mol of the compound of the formula (IV). To isolate the compounds of the formula (I), the solvent is distilled off and the residue is washed with water directly or after being taken up in organic solvent, in which case the organic phase is dried over sodium sulphate and freed from solvent in vacuo. The residue is appropriately purified by distillation or recrystallisation or by chromatography.

All the acids which give rise to physiologically acceptable salts can be used for such salt preparation. These acids include preferably, hydrogen halide acids, such as, for example, hydrochloric acid and hydrobromic acid, especially hydrochloric acid and furthermore phosphoric acid, nitric acid, sulphuric acid, monofunctional and bifunctional carboxylic acids and hydroxy-carboxylic acids, such as, for example acetic acid, maleic acid, succinic acid, fumaric acid, tartaric acid, citric acid, salicylic acid, sorbic acid, pamoic acid, lactic acid and sulphonic acids, such as, for example, p-toluenesulphonic acid and 1,5-naphthalenedisulphonic acid.

Salts of the compounds of the formula (I) can be obtained in a simple manner by customary methods of salt formation, for example by dissolving a compound of the formula (I) in a suitable inert solvent and adding the acid, for example hydrochloric acid, and they can be isolated in a known manner, for example by filtration, and if appropriate purified by washing with an inert organic solvent.

The compounds of the present invention display an anti-microbial action, in particular an antimycotic action. They possess a very broad antimycotic action spectrum, especially against dermatophytes and blastomyces as well as biphase fungi, for example against varieties of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton, such as *Trichophyton mentagrophytes*, varieties of Microsporon, such as, *Microsporon felineum* and varieties of Penicillium, such as *Penicillium commune*. This list of microorganisms in no way implies a limitation of the germs which can be combated but is only illustrative.

Examples which may be mentioned of fields of application in medicine are: dermatomycoses and systemic mycoses caused by Trichophyton mentagrophytes and other varieties of Trichophyton, varieties of Microsporon, Epidermophyton floccosum, blastomyces and biphase fungi as well as moulds.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compounds of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) absorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropraite, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

The invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, especially intravenously. Preferred pharmaceutical compositions and medicaments are therefore those adapted for administration such as parenteral administration. Administration in the method of the invention is preferably parenteral administration.

In general it has proved advantageous to administer orally amounts of from 10 mg to 300 mg/kg, preferably 50 mg to 200 mg/kg, of body weight per day to achieve effective results. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples A and B illustrate the in vitro and in vivo activity of compounds of the present invention.

EXAMPLE A

Antimycotic in vitro activity

Description of the experiment

The in vitro tests were carried out in a series dilution test with germ inocula of an average of $5 \times 10^4$ germs/ml of substrate. The nutrient medium was (a) for dermatophytes and moulds: Sabouraud's milieu d'epreuve and (b) for yeasts: meat extract/glucose broth.

The incubation temperature was 27° C. and the duration of incubation was 24 to 96 hours.

In these tests, the compound according to the invention show very good minimum inhibitory concentration values and thus prove superior to known compounds.

EXAMPLE B

Antimycotic in vivo activity (local) using experimental trichophytosis of guinea pigs as an example Description of the experiment White guinea pigs of the Pirbright-white strain were infected with a microconidia and macroconidia suspension of *Trichophyton mentagrophytes* on their shaven, non-scarified backs. The typical pattern of dermatophytosis with reddening, scaling and loss of hair up to total integumentary defect at the point of infection develops on untreated animals within 12 days after infection. The infected animals were treated locally once daily, starting on the 3rd day after infection, with 1% strength solutions of the preparations according to the invention in polyethylene glycol.

On the 14th day after infection, the untreated control animals showed the typical pattern of dermatophytosis, whilst preparation examples 1 and 3, for example, had completely inhibited the course of the infection.

The following Examples illustrate the production of compounds of the present invention.

EXAMPLES 1 and 2

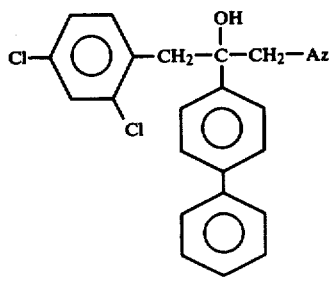

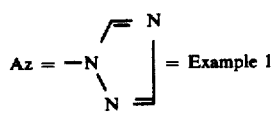

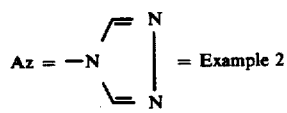

Process (b)

7.6 g (0.11 mol) of 1,2,4-triazole are added to a solution of 3.5 g (0.065 mol) of a sodium methylate in 18 ml of methyl alcohol; a solution of 19.5 g (0.05 mol) of 2-(4-biphenylyl)-3-chloro-1-(2,4-dichlorophenyl)-propan-2-ol in 38 ml of dimethylformamide is then added dropwise and the mixture is heated to 70° C. for 90 minutes. The solvent is removed in vacuo in a rotary evaporator and the residue is stirred with water. The resulting crystals are washed with diethyl ether and recrystallised from acetonitrile. 2.2 g of 2-(4-biphenylyl)-1-(2,4-dichlorophenyl)-3-(1,3,4-triazol-1-yl)-propan-2-ol of melting point 260° C. are obtained.

The acetonitrile solution (mother liquor) is evaporated and the resulting crystals are washed with diethyl ether and ethyl acetate. 6.5 g of 2-(4-biphenylyl)-1-(2,4-dichlorophenyl)-3-(1,2,4-triazol-1-yl)-propan-2-ol of melting point 124° C. are obtained.

Preparation of the starting material

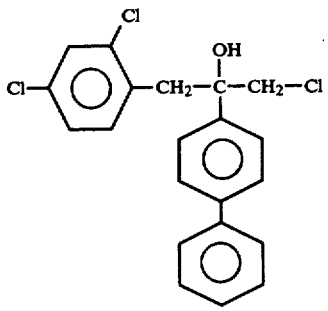

69.3 g (0.3 mol) of 4-phenylphenacyl chloride are added in portions to a solution of 0.6 mol of 2,4-dichlorobenzyl-magnesium chloride, obtained from 15.9 g (0.65 mol) of magnesium and 117.3 g (0.6 mol) of 2,4-dichlorobenzyl chloride in 300 ml of ether. The reaction mixture is then poured onto aqueous ammonium chloride solution and the ether phase is seperated off, washed with water, dried over sodium sulphate and evaporated. The oil which remains is extracted with petroleum ether and the petroleum ether solution is evaporated. The crystals are filtered off and dried. 62 g (53% of theory) of 2-(4-biphenylyl)-3-chloro-1-(2,4-dichlorophenyl)-propan-2-ol of melting point 84° C. are obtained.

EXAMPLES 3 AND 4

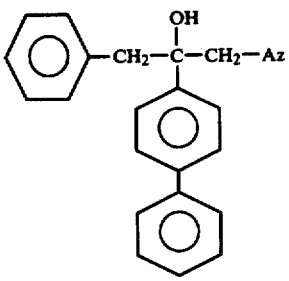

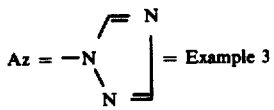

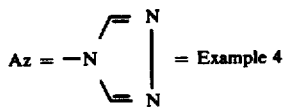

(Process b)

38.3 g (0.56 mol) of 1,2,4-triazole are added to a solution of 17.9 g (0.33 mol) of sodium methylate in 90 ml of methyl alcohol; a solution of 82 g (0.254 mol) of 2-(4-biphenyl)-3-chloro-1-phenyl-oropan-2-ol in 191 ml of dimethylformamide is then added dropwise and the mixture is heated to 60° C. for 90 minutes. The solvents are removed in vacuo in rotary evaporator, the residue is dissolved in methylene chloride and the solution is washed with water. The methylene chloride solution is dried over sodium sulphate and filtered and the filtrate is concentrated in vacuo. The resulting oil is seperated by chromatography. 13.8 g of 2-(4-biphenylyl)-1-phenyl-3-(1,2,4-triazol-1-yl)-propan-2-ol of melting point 124° C. and 2.7 g of 2-(4-biphenylyl)-1-phenyl-3-(1,3,4-triazol-1-yl)-propan-2-ol of melting point 246° C. are obtained.

Preparation of the starting material

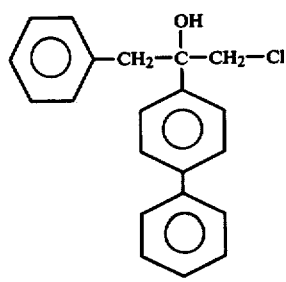

115.3 g (0.5 mol) of 4-phenylphenacyl chloride are added portions to a solution of benzyl-magnesium chloride, obtained from 24.3 g (1 mol) of magnesium and 115 ml (1 mol) of benzyl chloride in 150 ml of diethyl ether. The reaction mixture is warmed under reflux for 90 minutes and then poured onto aqueous ammonium chloride solution. The ether phase is separated off, washed with water, dried over sodium sulphate and concentrated. The oil which remains is made to crystallise by stirring with petroleum ether. 50 g (31% of theory) of 2-(4-biphenylyl)-3-chloro-1-phenylpropan-2-ol of melting point 96° C. are obtained.

The compounds in Table 1 below are obtained in a corresponding manner.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the animal's body to the active compound.

What is claimed is:

1. A hydroxypropyltriazole of the formula

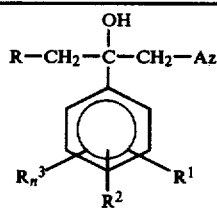

| Example No. | R | R$^1$ | R$^2$ | R$_n^3$ | Az | Melting point (°C.) or refractive index |
|---|---|---|---|---|---|---|
| 5 | –⟨⟩–Cl | 4–⟨⟩ | H | — | triazole (N=N, –N, =N) | 250 |
| 6 | –⟨⟩–Cl | 4–⟨⟩ | H | — | triazole | 104 |
| 7 | –⟨⟩–Cl | 4–⟨⟩–Cl | H | — | triazole | 144 |
| 8 | –⟨⟩–Cl | Cl, 4–⟨⟩ | H | — | triazole | 175 |
| 9 | –⟨⟩–Cl | Cl, 4–⟨⟩ | H | — | triazole | $n_D^{20}$: 1,5992 |
| 10 | –⟨⟩–Cl | Cl, 4–⟨⟩–Cl | H | — | triazole | 160 |
| 11 | –⟨⟩–Cl | Cl, 4–⟨⟩–Cl | H | — | triazole | |
| 12 | –⟨⟩–Cl | 4–⟨⟩–Cl | H | — | triazole | |

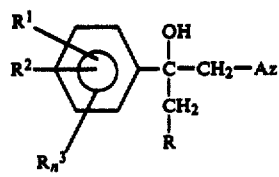

(I)

or a salt thereof,
in which
- Az denotes a 1,2,4-triazol-1-yl or 1,3,4-triazol-1-yl radical,
- R denotes phenyl, naphthyl or tetrahydronaphthyl radical which is unsubstituted or substituted by halogen, $C_1$-$C_4$-alkyl, $C_1$-$C_4$-alkoxy or halogenoalkyl with 1 to 4 carbon atoms and up to 5 halogen atoms,
- $R^1$ denotes a phenyl or $C_3$-$C_7$ cycloalkyl radical which is unsubstituted or substituted by halogen or $C_1$-$C_4$-alkyl and
- $R^2$ denotes a hydrogen atom, or
- $R^1$ and $R^2$ together, in the o-position relative to one another, represent an optionally halogen or $C_1$-$C_4$-alkyl substituted methylene bridge with 3 to 5 methylene groups, or, together with the phenyl ring, represent naphthyl,
- $R^3$ represents halogen, an alkyl or alkoxy group with in each case 1 to 4 carbon atoms or halogenoalkyl with 1 to 4 carbon atoms and up to 5 halogen atoms and
- n is 0, 1, 2 or 3.

2. A compound according to claim 1 in which Az denotes a 1,2,4-triazol-1-yl or 1,3,4-triazol-1-yl radical, R denotes a phenyl, naphthyl radical or tetrahydronaphthyl radical which is unsubstituted or substituted by halogen, $C_1$-$C_4$-alkyl, $C_1$-$C_4$-alkoxy or halogenoalkyl with 1 to 4 carbon atoms and up to 5 halogen atoms, $R^1$ denotes a phenyl or $C_3$ to $C_7$ cycloalkyl radical and $R^2$ denotes a hydrogen atom, or $R^1$ and $R^2$ together, in the ortho-position relative to one another, denote a methylene bridge which has 3 to 5 methylene groups and is optionally monosubstituted or polysubstituted by halogen or $C_1$-$C_4$-alkyl, or $R^1$ and $R^2$, together with the phenyl ring, complete a naphthyl radical; $R^3$ denotes a halogen atom, a straight-chain or branched alkyl or alkoxy group with in each case 1 to 4 carbon atoms, or a halogenoalkyl group with 1 to 4 carbon atoms and up to 5 halogen atoms, and n is 0, 1 or 2.

3. A compound according to claim 1 in which Az denotes a 1,2,4-triazol-1-yl or a 1,3,4-triazol-1-yl radical R denotes a phenyl radical which is optionally monosubstituted or disubstituted by chlorine, fluorine or methyl, or denotes a naphthyl or tetrahydronaphthyl radical, $R^1$ denotes a phenyl, cyclopentyl or cyclohexyl radical, which is optionally monosubstituted or disubstituted by chlorine, bromine, fluorine or methyl, and $R^2$ denotes a hydrogen atom, or $R^1$ and $R^2$ together, in the ortho-position relative to one another, denote a trimethylene, tetramethylene or pentamethylene bridge which is optionally substituted by chlorine or methyl or together with the phenyl ring, complete a naphthyl radical; $R^3$ denotes a chlorine or fluorine atom or a methyl group; and n is 0 or 1.

4. The compound of the formula

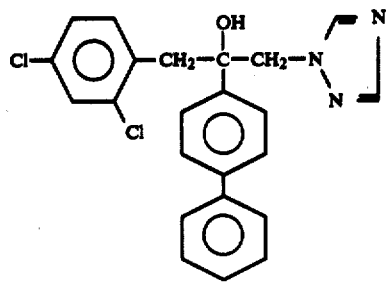

5. The compound of the formula

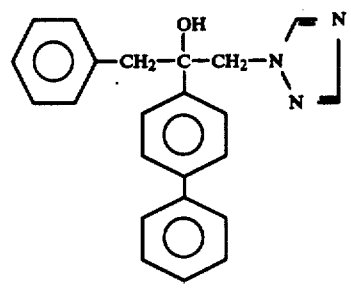

6. The compound of the formula

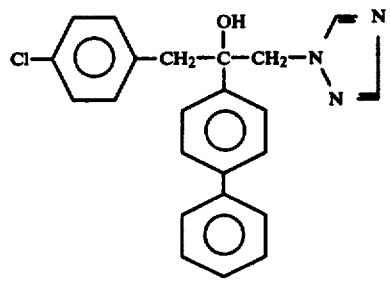

7. The compound of the formula

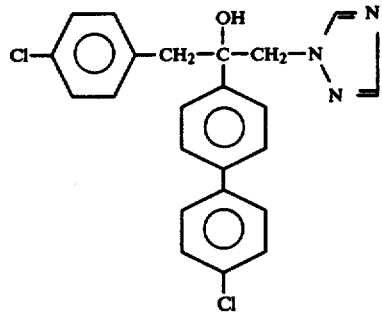

8. The compound of the formula

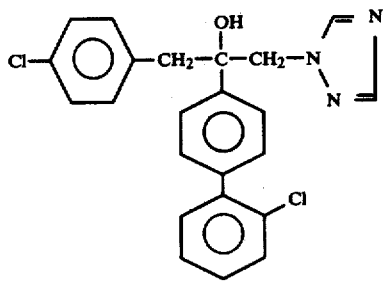

9. A pharmaceutical composition containing as an active ingredient an antimycotically effective amount of a compound according to claim 1 in admixture with a diluent.

10. A pharmaceutical composition of claim 9 in the form of a sterile or physiologically isotonic aqueous solution.

11. A composition according to claim 9 or 10 containing from 0.5 to 95% by weight of the said active ingredient.

12. A medicament in dosage unit form comprising an antimycotically effective amount of a compound according to claim 1 and an inert pharmaceutical carrier.

13. A medicament of claim 12 in the form of tablets, pills, dragees, capsules, ampoules, or suppositories.

14. A method of combating mycoses in warm-blooded animals which comprises administering to the animals an antimycotically effective amount of an active compound according to claim 1 either alone or in admixture with a diluent or in the form of a medicament.

15. A method according to claim 14 in which the active compound is administered in an amount of 50 to 200 mg per kg body weight per day.

16. A method according to claim 14 or 15 in which the active compound is administered parenterally.

* * * * *